United States Patent [19]

Guinot

[11] Patent Number: 4,593,020

[45] Date of Patent: Jun. 3, 1986

[54] THERAPEUTIC METHODS FOR THE TREATMENT OF HANGOVER

[75] Inventor: Philippe M. Guinot, Paris, France

[73] Assignee: Societe de Conseils de Recherches et d'Applications Scientifiques, Paris, France

[21] Appl. No.: 654,208

[22] Filed: Sep. 24, 1984

[30] Foreign Application Priority Data

Sep. 24, 1983 [GB] United Kingdom ............... 8325627

[51] Int. Cl.$^4$ ............... A61U 31/16; A61U 31/20; A61U 31/52; A61U 31/60
[52] U.S. Cl. ............... 514/159; 514/264; 514/556; 514/629; 514/811
[58] Field of Search ............ 514/556, 811, 159, 264, 514/629

[56] References Cited

FOREIGN PATENT DOCUMENTS 2590 3/1963 France .

OTHER PUBLICATIONS

Barak et al., "Betaine, Metabolic By-Product or Vital Methylating Agent?" Life Sciences, vol. 32, pp. 771-774, 1982.
Moyrand et al., "Les Troubles Fonctionnels de la Sphere Digestive Haute", M.C.D. vol. 7, pp. 453-457, 1978.

Primary Examiner—Stanley J. Friedman
Attorney, Agent, or Firm—Lucas & Just

[57] ABSTRACT

This invention relates to therapeutic compositions containing betaine salts for the treatment of hangover and for the lowering of alcohol content in blood in human. Daily dose comprises oral administration of 1 to 30 g, associated with appropriate carrier. Optional ingredients are an analgesic, a buffering agent and caffeine.

12 Claims, No Drawings

THERAPEUTIC METHODS FOR THE TREATMENT OF HANGOVER

BACKGROUND OF THE INVENTION

This invention relates to therapeutic compositions containing betaine salts.

Betaine, a quaternary nitrogen compound, is a metabolic byproduct of choline oxidation. Barak et al. (1983) Life Sciences 32, 771-774 suggests that betaine may serve as a methylating agent when normal methylating pathways are impaired by ethanol ingestion, drugs, or nutritional imbalances. Moyrand et al. (1978) M.C.D. 7, 453-457, describes the use of effervescing betaine citrate to treat patients suffering from dyspepsia and exhibiting symptoms including slow digestion, somnolence, and anorexia; betaine citrate, mixed with several additional ingredients, was administered in three 2 g doses daily for a minimum of 15 days and was found to be effective in the treatment of dyspeptic syndrome. French Patent No. 2590 M of 1963 describes the combination of less than one gram of betaine citrate with aspirin to buffer the aspirin.

SUMMARY OF THE INVENTION

In general, the invention features, in one aspect, a medicinal composition including a hangover symptom relieving amount of a pharmaceutically acceptable, non-toxic salt of betaine (preferably betaine citrate) alone or together with one or more of a pain relieving amount of an analgesic such as aspirin, a para-aminophenol derivative (preferably acetaminophen) or ibuprofen, an acid buffering amount of a buffering agent, and, optionally, an alertness inducing amount of caffeine.

In another aspect, the invention features a method of treating a human in need of relief of hangover symptoms comprising administering to the human a symptom relieving amount of a pharmaceutically acceptable, non-toxic salt of betaine.

In another aspect, the invention features a method of treating a human in need of the relief of symptoms related to ingestion of an alcoholic beverage including treatment of acute alcoholic intoxication and ethylic comas comprising administering to the human a symptom relieving amount of a pharmaceutically acceptable, non-toxic salt of betaine.

Preferably in the above methods the betaine salt, alone or together with the analgesic, caffeine, or buffering agent, is provided in admixture with a non-toxic, pharmaceutically acceptable carrier substance in the form of, e.g., a tablet, capsule, or liquid for oral administration.

The invention provides treatment for:
 hangover symptoms,
 undesirable symptoms associated with the presence of ethanol in the blood and
 lowering of blood ethanol level.

Other features and advantages of the invention will be apparent from the following description of the preferred embodiments thereof, and from the claims.

The activity of the composition according to the invention may be appreciated from the following experimentations:

I - HANGOVER

(a) DOSE/ACTIVITY PSYCHOMETRICS

Betaine Citrate or Placebo was administered to 6 healthy male volunteers both immediately (21H00) after and 11 hours (8H00, the day after), post ingestion of a standardized dose of alcohol (1.2 g ethanol/kg bodyweight in whisky taken between 20H00 and 20h30. Two dosing levels of Betaine Citrate (6 g and 12 g) were employed in a three-way crossover study which was carried out under double blind conditions. The treatment levels were allocated according to a randomized balanced latin square design. Psychometric testing was carried out pre-alcohol, one hour after the termination of the alcohol dose and 1 hour and 2.5 hours after the second dose of Betaine Citrate. This was administered on the morning of day 2 of each dosing stage. The dosing schedule is summarized as follows:

| | DOSAGE SCHEDULES | | |
|---|---|---|---|
| | Hours | | |
| | 20.00–20.30 | 21.00 | 08.00 |
| A | Alcohol | Placebo | Placebo |
| B | Alcohol | Betaine Citrate (6 g) | Betaine Citrate (6 g) |
| C | Alcohol | Betaine Citrate (12 g) | Betaine Citrate (12 g) |

Subjects were assigned to the dosage schedules according to the following randomised balanced latin square.

| Subject No. | Period 1 | Period 2 | Period 3 |
|---|---|---|---|
| 1 | A | B | C |
| 2 | B | C | A |
| 3 | C | A | B |
| 4 | A | C | B |
| 5 | C | B | A |
| 6 | B | A | C |

Analysis

Statistical analysis of the psychometric data consisted of a two-way Analysis of Variance (Treatments x Times) with repeated measures on the times factor. This analysis was supplemented by a series of t-tests which utilized difference scores. Thus, differences from pre-dose values at each testing time post dose for the active dosing groups were compared with the corresponding difference scores for the alcohol+placebo group. In this way any changes from pre-dose values for the alcohol and Betaine Citrate groups would be identified if they differed to a statistically significant extent from the corresponding change from pre-dose scores for the alcohol and placebo group.

Results

The two-way Analysis of Variance of the performance and mood variables identified significant main effects for the Critical Flicker Fusion measure on the "Dose" factor. Significant differences were also found to exist on the "Times" factor for Simple Reaction Time and for the Finger Dexterity Test, Level 1. The absence of "Interaction" effects however suggests that there is no overall difference between the dose response profiles for the active and placebo groups. Thus, the direction of the changes in the performance and mood scale scores is for the most part consistent across each of the three treatments.

The t-test analysis of the difference scores indicates however that the extent of the impairment after the alcohol dose does differ across the respective dosing stages. Subjects scored significantly lower on the Hand Tremor test, 1 hour after receiving alcohol and Betaine Citrate (6 g and 12 g) than they scored 1 hour after receiving alcohol and placebo.

Similarly, subjects rated themselves more "contented" and more "tranquil" 1 hour after alcohol and Betaine Citrate (12 g) than they did 1 hour after receiving alcohol and placebo. Subjects also rated themselves more "happy" 2.5 hours after ingestion of the second dose of Betaine Citrate (12 g) than they did at the corresponding test session after receiving placebo.

Further inspection of the data indicates that subjects were less impaired 1 hour following alcohol and Betaine Citrate than they were after receiving alcohol and placebo for another five of the performance test measures (Simple Reaction Time, Critical Flicker Fusion, Finger Dexterity Test (Level One), Digit Copying and Mental Arithmetic). The effect also appeared to be dose-related, being more evident following the 12 g dose of Betaine Citrate than following 6 g.

(b) EFFECTS OF BETAINE AND ANALGESIC THE MORNING AFTER ALCOHOL ADMINISTRATION

One way of comparing the effects of betaine and analgesic the morning after alcohol administration is to look at the changes in subjective assessment of mental state together with actual measures of performance efficiency before and after the administration of the two substances.

For an overall comparison of the four treatments—analgesic & betaine citrate 6 g (D), placebo analgesic & betaine citrate 6 g (E), analgesic & placebo-betaine (F), placebo-analgesic & placebo-betaine (G)—a simple ranking of the changes over the morning will give us an indication of the relative efficacies of these treatments, taking into consideration: attentional efficiency, memory, and subjective assessments of mental state.

Of the measures of attentional efficiency, the speed of reaction in the raid information processing test was the most statistically significant (F=23.8, dg=3,165, p<0.00001). The two measures of memory were both highly significant (F=34.9, df=3,165, p<0.000001; and F=69.5, df=3,209, p<0.0000001, respectively). Of the subjective assessments, alertness was the most reliable (F=13.1, df=3,165, p<0.0001). The changes in each of the four conditions following the treatments are presented below for each of these measures, together with the rankings.

This experimentation was undertaken three times with the same conditions of alcohol intake and hours of treatment as above; in the first experimentation, analgesic was acetyl salicylic acid (1 g), in the second, paracetamol (0.66 g) and in the third ibuprofen (0.8 g). As the results of these three experimentations lead to the same final ranking, only the first one is described in details.

| | RANKINGS | | | | | | | |
|---|---|---|---|---|---|---|---|---|
| | D | E | F | G | D | E | F | G |
| Reaction Time- | 19 | 24 | 18 | 13 | 2 | 1 | 3 | 4 |
| msec (increase in speed following treatment) | | | | | | | | |
| Memory - number of words recalled (change + or − following treatment) | | | | | | | | |
| Immediate recall | 0.8 | 0.4 | 0.8 | −1.3 | 1.5 | 3 | 1.5 | 4 |
| Delayed recall | −0.4 | −1.1 | −0.4 | −2.6 | 1.5 | 3 | 1.5 | 4 |
| Self rated alertness mm (Increase in alertness following treatment) | 11.2 | 13.4 | 8.6 | 4.6 | 2 | 1 | 3 | 4 |
| MEAN RANKINGS | | | | 1.75 | 2.0 | 2.25 | 4.0 |

Friedman's Two Way ANOVA by ranks was applied to the data and yielded a value of Chi=7.5, df=3, which only just missed significance at the 5% level (7.82) but was much higher than the value for the 10% level (6.25), and thus shows an interesting trend.

This analysis has therefore shown that the relative efficiency of the three series of four treatments is in the following order:
1. Betaine and analgesic
2. Betaine alone
3. Analgesic alone
4. Neither Betaine nor analgesic

II - BIOCHEMISTRY (a) DOSE/ACTIVITY

For the various biochemistry parameters investigated in this study, the following plasma variables were selected for statistical analysis: Ethanol, Lactate, Acetaldehyde, Ketone Bodies, High Density Lipoproteins, Low Density Lipoproteins.

For each variable the data were subjected to a two-way analysis of variance (treatment×time) with repeated measures on the subjects. The results were then further investigated by a series of t tests utilizing difference scores. In this analysis changes from pre-dose values at each post dose testing time for the group which received alcohol+placebo, were compared with the corresponding changes for the groups receiving alcohol+betaine citrate (6 g and 12 g).

Results

The two-way analysis of variance identified significant "treatment" effects only for plasma ethanol and ketone bodies. The results reflect significant overall differences between the three treatments for these variables. Statistically significant "time" effects were also evident for ethanol, ketone bodies and acetaldehyde. However no significant "treatment×time" interactions were observed indicating that the dose response profiles were in a similar direction.

The t-test analysis of the difference scores identified a significant (p 0.05) reduction in plasma ethanol for subjects who received alcohol+12 g betaine citrate as compared to subjects receiving alcohol+placebo, one hour after completion of the alcohol intake. The mean peak plasma ethanol values for the three treatments were:

Alcohol+Placebo: 107.3 mg %
Alcohol+6 g Betaine Citrate: 91.3 mg %
Alcohol+12 g Betaine Citrate: 69.8 mg % so that the observed trend is clearly dose related.

The corresponding t-test analysis for the other investigated variables (ketone bodies and acetaldehyde) did not reveal similar treatment associated changes.

(b) BLOOD ALCOHOL VALUES

Another experimentation has been conducted for the determination of the blood alcohol values in relationship with the treatments.

For this experimentation, 2 groups of each 6 subjects have been treated orally, a quarter of an hour after a common alcohol intake of 1.2 g/kg of whisky as follows:

the first group receives a single dose 6 g of betaine citrate and the second group receives a single dose 6 g of placebo.

Samples of blood were collected at various times after the end of the alcohol intake and the subsequent treatment. The results appear on the following table:

|  | CONDITION | |
|---|---|---|
|  | H | J |
|  | Blood Alcohol (mg %) | |
| 15 min | 98.6 | 99.8 |
| 30 min | 128.8 | 146.4 |
| 45 min | 129.4 | 142.5 |
| 1 hour | 129.6 | 142.3 |
| 1.5 hour | 111.2 | 122.8 |
| 2 hours | 102.7 | 116.5 |
| 3 hours | 84.1 | 102.8 |
| 4 hours | 69.3 | 81.8 |

It appears clearly from these figures that betaine citrate administration lowers the alcohol content of blood.

DESCRIPTION OF THE PREFERRED EMBODIMENTS

We turn now to a description of preferred embodiments of the invention.

Composition

A betaine salt, according to the invention, is ordinarily provided admixed with a non-toxic, pharmaceutically acceptable carrier substance as such, or in combination with an effective amount of one or more of analgesic such as acetyl salicylic acid, a para-aminophenol derivative, ibuprofen, a buffering agent and, optionally, caffeine. These additional ingredients, all of which are found in conventional pain or discomfort-relieving preparations, are administered in combination with the betaine salt, in conventional dosages for those substances.

These substances all exhibit short-term, acute effects, and they are thus appropriately administered in combination with a betaine salt which, according to the invention, also exhibits acute, as opposed to chronic, symptom-relieving effects.

Although the preferred betaine salt is betaine citrate, other salts, e.g. betaine/HCl and betaine aspartate, can also be used. Betaine citrate is preferable because, in addition to the therapeutic benefits conferred by betaine, the citrate provides desirable buffering of acid, in some instances obviating the use of additional acid buffering agent. In other instances, particularly where a para-aminophenol analgesic is being administered concurrently with betaine citrate, additional buffering agent, e.g. sodium citrate, is desired.

The dosage of betaine salt to be administered in an individual case will vary with factors such as the amount of ethanol contained in the ingested beverage and the metabolism of the individual. In general, the preferred daily adult dose contains about 1–24 g betaine salt, preferably 4–16 g, most preferably about 12 g. Provided in combination with the betaine salt are, optionally, one or more of: 100 mg to 400 mg of acetyl salicylic acid, 100 mg to 325 mg of a para-aminophenol derived analgesic, preferably acetaminophen; 50 mg to 200 mg of caffeine; and 1 g to 4 g of a buffering agent, preferably sodium citrate. The betaine citrate can also be provided in combination wioth an effervescing agent. When combining betaine citrate with a para-aminophenol derived analgesic, for the sake of stability, the pH of the mixture, about 2.3, should be raised to about 5.2 using a sufficient amount of the buffering agent.

Although acetaminophen (paracetamol) is the preferred para-aminophenol derived analgesic, others, e.g. phenacetin, acetanilide or acetaminosalol may be used.

In addition to buffering agents, caffeine, acetyl salicylic acid and para-aminophenol derived analgesic, the compositions of the invention can optionally contain other ingredients as well, to provide desired properties such as texture, color, flavor, and effervescence. Examples of such additional ingredients are sorbitol, methyl or propyl parahydroxybenzoate, essence of lemon, glucose, lactose, sucrose, mannitol, sorbic acid, saccharin, artificial aromas, polyethylene glycol, bicarbonate of soda, sodium saccharinate, sodium alginate, benzoic acid, erythrosin, cellulose, polyvinylpyrrolidone, talc, magnesium stearate, sodium hydroxide and silicic acid.

Example of betaine salt-containing compositions of the invention are given below.

| Ingredients | Amount |
|---|---|
| Composition 1: effervescent tablet | |
| Betaine Citrate | 3.000 g |
| Sodium Citrate | 0.690 g |
| Anhydrous Citric Acid | 0.057 g |
| Sucrose | 0.348 g |
| Sodium Saccharinate | 0.012 g |
| Polyethyleneglycol | 0.084 g |
| Aroma of Lemon | 0.003 g |
| Aroma of Orange | 0.006 g |
| Composition 2: gel (bags) | |
| Betaine Citrate | 2.000 g |
| Saccharin | 0.010 g |
| Sodium Alginate | 0.400 g |
| Benzoic Acid | 0.010 g |
| Artificial Aroma | 0.020 g |
| Erythrosin | 0.0005 g |
| Composition 3: capsule/tablet | |
| Betaine Citrate | 0.400 g |
| Ibuprofen | 0.100 g |
| Silicic Acid | 0.005 g |
| Magnesium Stearate | 0.010 g |
| Composition 4: soluble powder (bags) | |
| Betaine Citrate | 2.000 g |
| Acetyl salicylic acid | 0.200 g |
| Caffeine Citrate | 0.250 g |
| Sodium Saccharinate | 0.015 g |
| Sorbitol | 2.600 g |
| Composition 5: effervescent powder (bags) | |
| Betaine Citrate | 6.000 g |
| Acetaminophen | 0.100 g |
| Caffeine | 0.050 g |
| Citric Acid | 0.100 g |
| Sodium Bicarbonate | 0.500 g |

| Ingredients | Amount |
|---|---|
| Sodium Saccharinate | 0.010 g |
| Sucrose | 2.315 g |
| Composition 6: tablet | |
| Betaine Citrate | 0.250 g |
| Phenacetin | 0.050 g |
| Saccharin | 1.150 g |
| Mannitol | 0.750 g |
| Lactose | 0.200 g |
| Magnesium Stearate | 0.050 g |
| Composition 7: capsules | |
| Anhydrous Betaine Citrate | 0.200 g |
| Phenacetin | 0.050 g |
| Lactose | 0.060 g |
| Pure cellulose | 0.040 g |
| Reticulated polyvinylpyrrolidone | 0.010 g |
| Magnesium Stearate | 0.010 g |
| Composition 8: drop solution (100 ml bottle: daily dose) | |
| Anhydrous Betaine Citrate | 16.000 g |
| Acetaminophen | 0.325 g |
| Caffeine | 0.100 g |
| 95% Ethanol | 1.000 ml |
| Sodium saccharinate | 0.020 g |
| Artificial Aroma | 0.040 g |
| Sodium Hydroxide, sufficient amount for pH 5.2 | |
| Purified water, sufficient amount for 100 ml. | |
| Composition 9: syrup (bottle of 15 ml: daily dose) | |
| Anhydrous Betaine Citrate | 5.0000 g |
| Acetaminophen | 0.2100 g |
| Caffeine | 0.1200 g |
| Sucrose | 6.0000 g |
| Sodium Saccharinate | 0.0120 g |
| 95% Ethanol | 1.5000 ml |
| Methyl Parahydroxybenzoate | 0.0096 g |
| Propyl Parahydroxybenzoate | 0.0024 g |
| Artificial Aroma | 0.0300 g |
| Artificial Orange Color | 0.0003 g |
| Aqueous sodium Hydroxide (30 g/100 ml), sufficient amount for pH 5.2. | |
| Composition 10: drop solution (4 ml phial) | |
| Anhydrous Betaine Citrate | 1.200 g |
| Phenacetin | 0.160 g |
| Caffeine | 0.110 g |
| 95% Ethanol | 1.000 ml |
| Sodium Saccharinate | 0.025 g |
| Artificial Aroma | 0.050 g |
| Sodium Hydroxide, sufficient amount for pH 5.2 | |
| Composition 11: effervescent powder (bag) | |
| Betaine Citrate | 2.000 g |
| Acetanilide | 0.150 g |
| Caffeine | 0.060 g |
| Citric acid | 0.120 g |
| Sodium Bicarbonate | 0.400 g |
| Sodium Saccharinate | 0.020 g |
| Lactose | 5.040 g |
| Composition 12: effervescent powder (bags) | |
| Betaine Citrate | 2.000 g |
| Acetyl salicylic acid | 0.200 g |
| Caffeine Citrate | 0.150 g |
| Sodium Bicarbonate | 0.500 g |
| Sodium Saccharinate | 0.015 g |
| Lactose | 3.000 g |
| Artificial Aroma | 0.050 g |
| Composition 13: soluble powder (bag) | |
| Betaine Citrate | 1.000 g |
| Acetaminosalol | 0.320 g |
| Caffeine Citrate | 0.150 g |
| Sodium Saccharinate | 0.020 g |
| Sorbitol | 2.500 g |
| Composition 14: gel (bags) | |
| Betaine Citrate | 2.000 g |
| Acetaminosalol | 0.250 g |
| Saccharin | 0.040 g |
| Sodium Alginate | 0.200 g |
| Artificial Aroma | 0.030 g |
| Composition 15: gel (bags) | |
| Betaine Citrate | 2.000 g |
| Acetyl salicylic Acid | 0.110 g |
| Saccharin | 0.010 g |
| Sodium Alginate | 0.400 g |
| Artificial Aroma | 0.025 g |
| Composition 16: soluble powder (bag) | |
| Betaine Citrate | 2.000 g |
| Ibuprofen | 0.150 g |
| Caffeine Citrate | 0.150 g |
| Sodium Saccharinate | 0.050 g |
| Sorbitol | 2.000 g |
| Composition 17: effervescent tablet | |
| Betaine Citrate | 3.000 g |
| Caffeine Citrate | 0.150 g |
| Sodium Citrate | 0.500 g |
| Anhydrous Citric Acid | 0.057 g |
| Glucose | 0.400 g |
| Sodium Saccharinate | 0.020 g |
| Polyethyleneglycol | 0.060 g |
| Composition 18: effervescent tablet | |
| Betaine Citrate | 3.000 g |
| Acetaminophen | 0.150 g |
| Caffeine | 0.100 g |
| Sodium Citrate | 0.690 g |
| Anhydrous Citric Acid | 0.057 g |
| Glucose | 0.400 g |
| Polyethyleneglycol | 0.084 g |
| Aroma of Orange | 0.006 g |
| Sodium Hydroxide, sufficient amount for pH 5.6 | |
| Composition 19: effervescent tablet | |
| Betaine Citrate | 1.750 g |
| Acetyl salicylic acid | 0.250 g |
| Sodium Bicarbonate | 1.500 g |
| Saccharin Sodium | 0.003 g |
| Lubricant (Stearic Acid/Magnesium stearate Mixture - 10/1 ratio) | 0.002 g |
| | 0.002 g |
| | 3.505 g |

Use

Betaine salt is orally administered, according to the invention.

To treat symptoms related with the ingestion of alcoholic beverages (hangover Syndrome), betaine salt is administered in single doses of 1-24 g, preferably 4-16 g, most preferably about 12 g, between one and five times per day.

Hangover symptoms are associated with recent overindulgence with alcoholic beverages. In general, hangover symptoms occur when at least about three hours, and not more than about two days, have elapsed since the ingestion of said alcoholic beverages. It is during this time period, when the hangover symptoms are present, but the ethanol has been largely metabolized, that the administration of betaine salt to treat hangover symptoms is carried out.

I claim:

1. A method of treating a human in need of relief of hangover symptoms resulting from overindulgence of ethanol, said method comprising orally administering to said human a therapeutically effective amount of an admixture comprising betaine citrate and a pharmaceutically acceptable carrier.

2. A method of treating a human suffering from symptoms associated with ethanol in the bloodstream comprising orally administering to said human a therapeutically effective amount of an admixture comprising betaine citrate and a pharmaceutically acceptable carrier.

3. A method of treating a human in need of relief of hangover symptoms resulting from overindulgence of ethanol, said method comprising orally administering to said human an admixture comprising a therapeutically effective amount of betaine citrate together with a pharmaceutically acceptable carrier.

4. A method of treating a human suffering from symptoms associated with ethanol in the bloodstream comprising orally administering to said human an admixture comprising a therapeutically effective amount of betaine citrate together with a pharmaceutically acceptable carrier.

5. The method of claim 3 wherein said admixture is in the form of a tablet, capsule, or liquid.

6. The method of claim 3 wherein said betaine citrate is administered in a daily dose of 1 to 30 g.

7. The method of claim 6 wherein said betaine citrate is administered in a daily dose of 6 to 12 g.

8. The method of claim 4 wherein said betaine citrate is administered concurrently with the ingestion of ethanol by said human.

9. A method of treating a human suffering from symptoms associated with ethanol in the bloodstream comprising orally administering to said human a blood alcohol reducing amount of betaine citrate.

10. The method of claim 4 wherein said admixture is in the form of a tablet, capsule, or liquid.

11. The method of claim 4 wherein said betaine citrate is administered in a daily dose of 6 to 12 g.

12. The method of claim 1 wherein said admixture also includes one or more of (a) a pain relieving amount of analgesic selected from within the group of acetyl salicylic acid, a para-aminophenol derivative and ibuprofen, (b) an acid buffering amount of a buffering agent, and (c) an alertness inducing amount of caffeine.

* * * * *